United States Patent [19]

Fletcher

[11] 4,223,995
[45] Sep. 23, 1980

[54] CALIBRATION SYSTEM FOR SPECTROPHOTOMETERS

[76] Inventor: Taylor C. Fletcher, 1534 Sunny Crest Dr., Fullerton, Calif. 92635

[21] Appl. No.: 935,868

[22] Filed: Aug. 22, 1978

[51] Int. Cl.³ ............................. G01J 3/48; G01J 3/42
[52] U.S. Cl. .................................... 356/418; 356/320; 356/243
[58] Field of Search ............... 356/308, 309, 319–330, 356/418, 419, 243

[56] References Cited

U.S. PATENT DOCUMENTS

| | | | |
|---|---|---|---|
| 3,762,817 | 10/1973 | Harklau | 356/419 |
| 3,844,661 | 10/1974 | Birkett et al. | 356/418 |

Primary Examiner—Vincent P. McGraw

Attorney, Agent, or Firm—Keith D. Beecher

[57] ABSTRACT

A calibration system is provided for spectrophotometers of the type in which two or more wave lengths of light are caused to be transmitted through a sample cell. The calibration system may be used to calibrate spectrophotometers in which the beams are sequentially transmitted through the sample. In the practice of the invention, the sample is replaced with a number of accurately known optical attenuators which are introduced into the system in synchronism with the two light beams. The system provides calibration for both the scaling and linearization of the spectrophotometer, or conversely provides for the generation of tables and graphs which permit the operator to correct the photometer reading into an accurate representation.

14 Claims, 13 Drawing Figures

CALIBRATION SYSTEM FOR SPECTROPHOTOMETERS

BACKGROUND

Spectrophotometric analysis is a method of chemical analysis based on the absorption or attenuation by different substances of light of a specified wave length. The instruments used to perform such an analysis are referred to as spectrophotometers. The sequential dual wave length spectrophotometer uses a common light path to cause two light beams to be transmitted through the sample sequentially at two different wave lengths, one of the light beams being the reference beam ($I_R$) which establishes reference thresholds for the other beam ($I_S$).

There is a need in spectrophotometers to determine the sensitivity of the instrument and to correct for errors introduced into the spectrophotometer readings due to imperfections in the components which make up the system. One error which arises is due to non-linearities in the spectrophotometer detector. Photomultiplier tubes, which usually constitute the spectrophotometer detector, for example, become non-linear at large anode currents. Another error is caused by off-sets in the detector. For example, the dark current in a photomultiplier tube adds a fixed amplitude to its output signal. In addition, the electronic circuitry which is used to sense and process the output signal from the detector often has inherent non-linearities and zero off-sets which create photometric reading errors.

The principal object of the present invention, as stated above, is to provide a suitable system for calibrating spectrophotometers so that the aforesaid scaling and linearization errors may be compensated.

DETAILED DESCRIPTION OF THE ILLUSTRATED EMBODIMENTS

Figure 1:
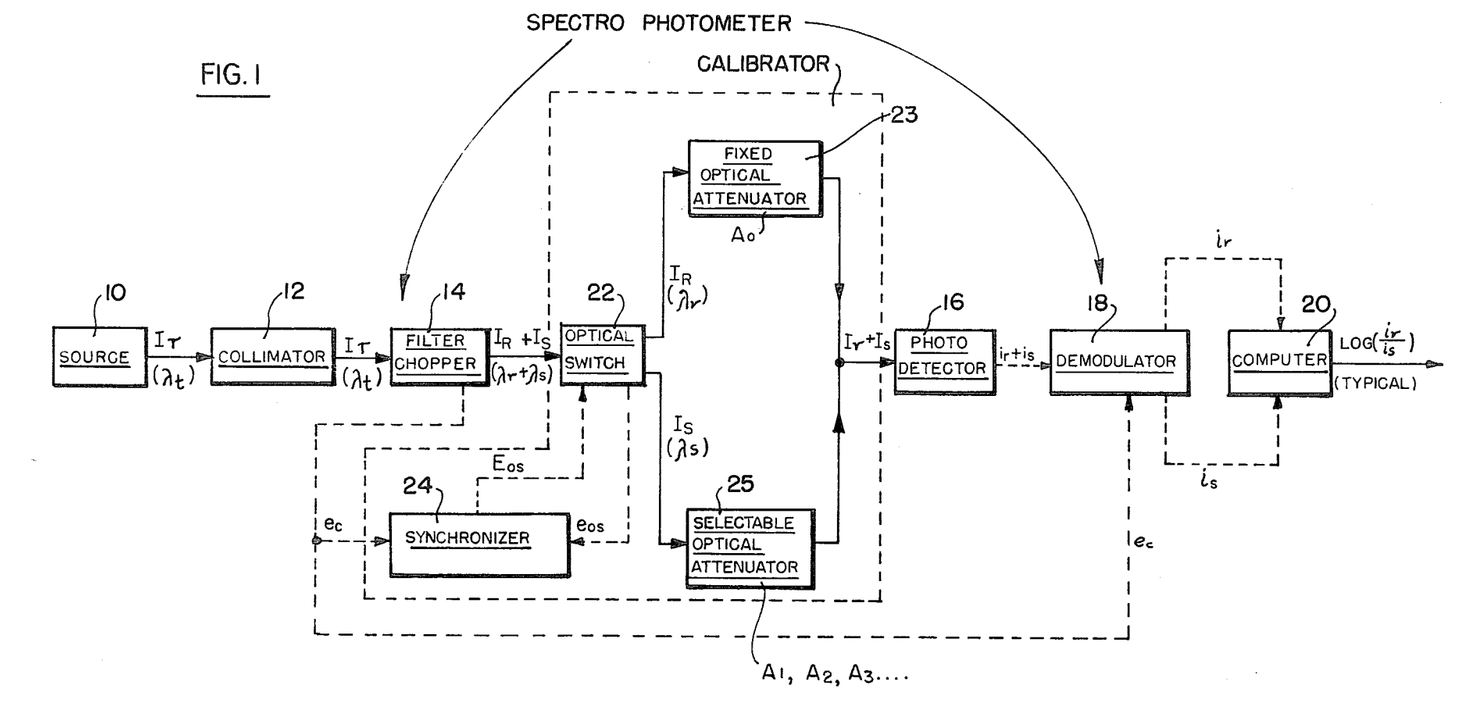
FIG. 1 is a block diagram of a typical dual wave length, or bichromatic, spectrophotometer, in which the sample has been replaced by a calibrating system in accordance with the concepts of the invention.

The spectrophotometer system shown in FIG. 1 includes a light source 10 which generates a white light beam ($I_T$) at a mean wave length ($\lambda_t$). The light beam from source 10 is passed through a collimator 12 and the collimated white light beam $I_T$ at a mean wave length ($\lambda_t$) from the collimator is passed through a filter chopper 14 which produces two light beams at two selected wave lengths, specifically a first light beam ($I_R$) which is the reference beam, and which has a wave length ($\lambda_t$), and a second light beam ($I_S$) which is the sample beam, and which has a wave length ($\lambda_s$). For calibration purposes, $\lambda_s$ may be the same as $\lambda_r$.

For convenience, the two light beams at the entrance to the calibration system will be referred to as $I_R$ and $I_S$. Likewise, the two beams as they emerge from the calibration system, for convenience, will be referred to as $I_r$ and $I_s$.

The beams $I_r$ and $I_s$ are detected by a detector 16 which may, for example, be in the form of a photomultiplier, and the resulting electrical currents $i_r$ and $i_s$ corresponding to the two beams are introduced to a synchronous demodulator 18, which separates the two currents, and which introduces them to a computer 20, all of the aforesaid components being incorporated into the spectrophotometer. The demodulator 18 is driven by a signal $e_c$ derived from the filter chopper 14, so that it may operate in synchronism with the filter chopper.

Typically the attenuation of the light beams by the material in the sample cell is much greater at the sample wave length ($\lambda_s$), than it is at the reference wave length ($\lambda_r$). The change of the intensity ratio of the two light beams $I_R$ and $I_S$ when a sample is introduced into the sample cell is a measure of the concentration of the material being measured. Because of the spectrophotometer configuration, errors due to source, detector and optics variations with time are reasonably cancelled out. However, the errors discussed above are not eliminated and require special calibration or adjustments, as will be effectuated by the calibration system of the present invention.

Figures 5, 6:
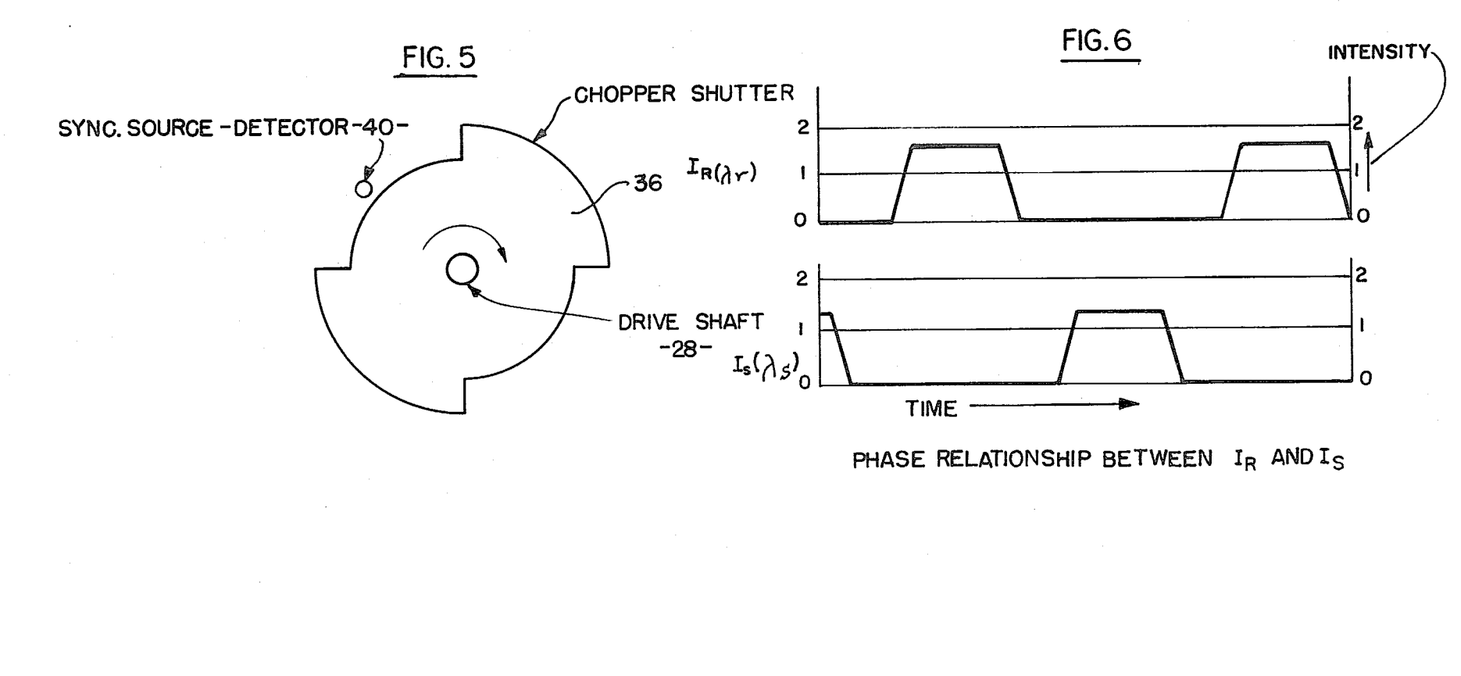
FIG. 5 is a schematic plan view of a synchronizing optical chopper mechanism used in the system of FIG. 2.
FIG. 6 is a pair of curves showing the relationship between the reference beam ($I_R$) and the sample beam ($I_S$) in the system of FIG. 1.

The spectrophotometer of FIG. 1, with the sample in place, alternately passes the reference light beam ($I_R$) and the sample light beam ($I_S$) through the sample cell with a dark period between each transition (see FIG. 6). The detector output ratio is a measure of the concentration of the unknown substance in the sample cell. The light beam intensities $I_R$ and $I_S$ are sensed in the common detector 16, and are converted respectively into the electric currents $i_r$ and $i_s$. As stated above, the electric currents $i_r$ and $i_s$ are separated from each other in time by the quiescent periods which occur during the dark periods between light beam segments, and are directed to separate electrical curcuits by the synchronous demodulator 18.

Typically, the computer 20 in the spectrophotometer system will perform the calculation $\log(i_r/i_s) - \log(i_{ro}/i_{so})$ as this output is approximately proportional to the concentration of the material to be measured in the sample cell. The currents $i_{ro}$ and $i_{so}$ are generated by the detector 16 with no unknown substance in the sample cell; whereas the currents $i_r$ and $i_s$ are generated by the detector with the unknown substance in the sample cell. The detector output ratio $$\frac{i_r/i_s}{i_{ro}/i_{so}}$$

is a measure of the concentration of the unknown in the sample cell.

Figure 4:
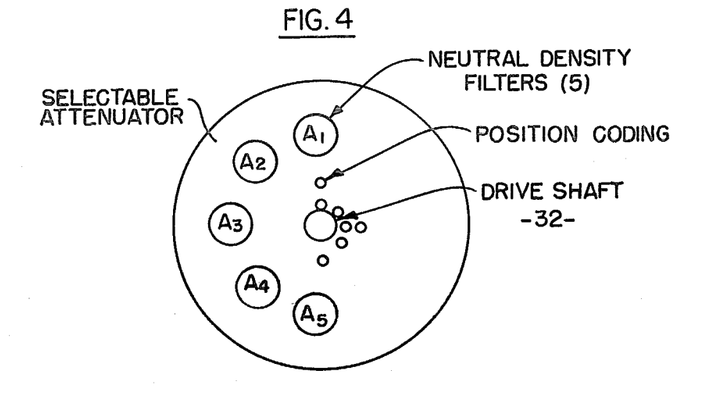
FIG. 4 is a schematic plan view of a variable optical attenuator used in the system of FIG. 2.

In the practice of the present invention, and as shown in FIG. 1, for example, the sample is replaced with a pair of attenuators 23 and 25. Attenuator 23 is fixed, and it includes a single neutral density optical filter $A_0$; whereas, attenuator 25 (FIG. 4) is adjustable, and it contains a number of neutral density optical filters $A_1$, $A_2, A_3 \ldots$. The attenuation values of all the filters are known. An optical switch 22 is provided in the calibration system which directs the reference beam $I_R$ to the attenuator 23; and directs the sample beam $I_S$ to the optical attenuator 25. Each of the filters of attenuator 25 may be selectively placed in the path of the light beam. The outputs $I_r$ and $I_s$ from the attenuators 23 and 25 are introduced to the detector 16.

If the fixed optical attenuator 23 is placed in the light beam when $I_R$ is passing through the system, and if the selectively adjustable attenuators 25 are introduced into the light beam when $I_S$ is passing through the system, a series of ratios $I_r/I_s$ can be obtained. If the attenuation values are known, it is then possible to calibrate the spectrophotometer. The spectrophotometer is calibrated in the following sequence of steps:

(1) A base of zero condition is set by passing the light beam $I_R$ through the attenuator filter $A_0$ giving $I_{ro}$, and the light beam $I_S$ through the attenuator filter $A_1$ giving $I_{so}$. The attenuator filters $A_0$ and $A_1$ are usually low value attenuators, and may be equal, or one or both may be non-existent, so that no attenuation is provided for this particular step. The spectrophotometer is then adjusted to read an absorbance of zero, or a transmittance of 100%.

(2) The light beam $I_R$ is passed through the fixed attenuator filter $A_0$ giving $I_r$, while the light beam $I_S$ is passed through the adjustable attenuator filter $A_2$ giving $I_s$. Since the ratio of the attenuator filters $A_1$ and $A_2$ is known, the gain of the spectrophotometer can now be set. Note that while $I_{ro}$ and $I_r$ appear to be equal, variations in source intensity, etc., will cause them to be different, thus requiring the measurement of $I_r$.

(3) The reference beam $I_R$ is passed through the fixed attenuator filter $A_0$ giving $I_r'$, while the sample beam $I_S$ is passed through the adjustable attenuator filter $A_3$ whose attenuation is greater than the Filter $A_2$ giving $I_s$, and the attenuation of filter $A_2$ is, in turn, greater than the attenuation of filter $A_1$. In this case the sample light beam $I_s$ emitted by the calibrator will be quite small, and the zero off-set in the electronics and dark current in the photomultiplier detector 16 usually becomes significant. Typically, an off-set adjustment in the electronics can be made to eliminate this error. In practice, steps 2 and 3 are usually interactive and require repeated adjustments to accomplish the desired system performance.

It should be noted that adding additional attenuator ratios can allow correction of additional non-linearities in the system. Also, adding a common attenuator in series to both the $I_R$ and $I_S$ light beams will maintain the same ratio of $I_R/I_S$, but the spectrophotometer will be operating in a different, but known condition. Such information can be used for additional adjustments or calibration curves.

Figure 2:
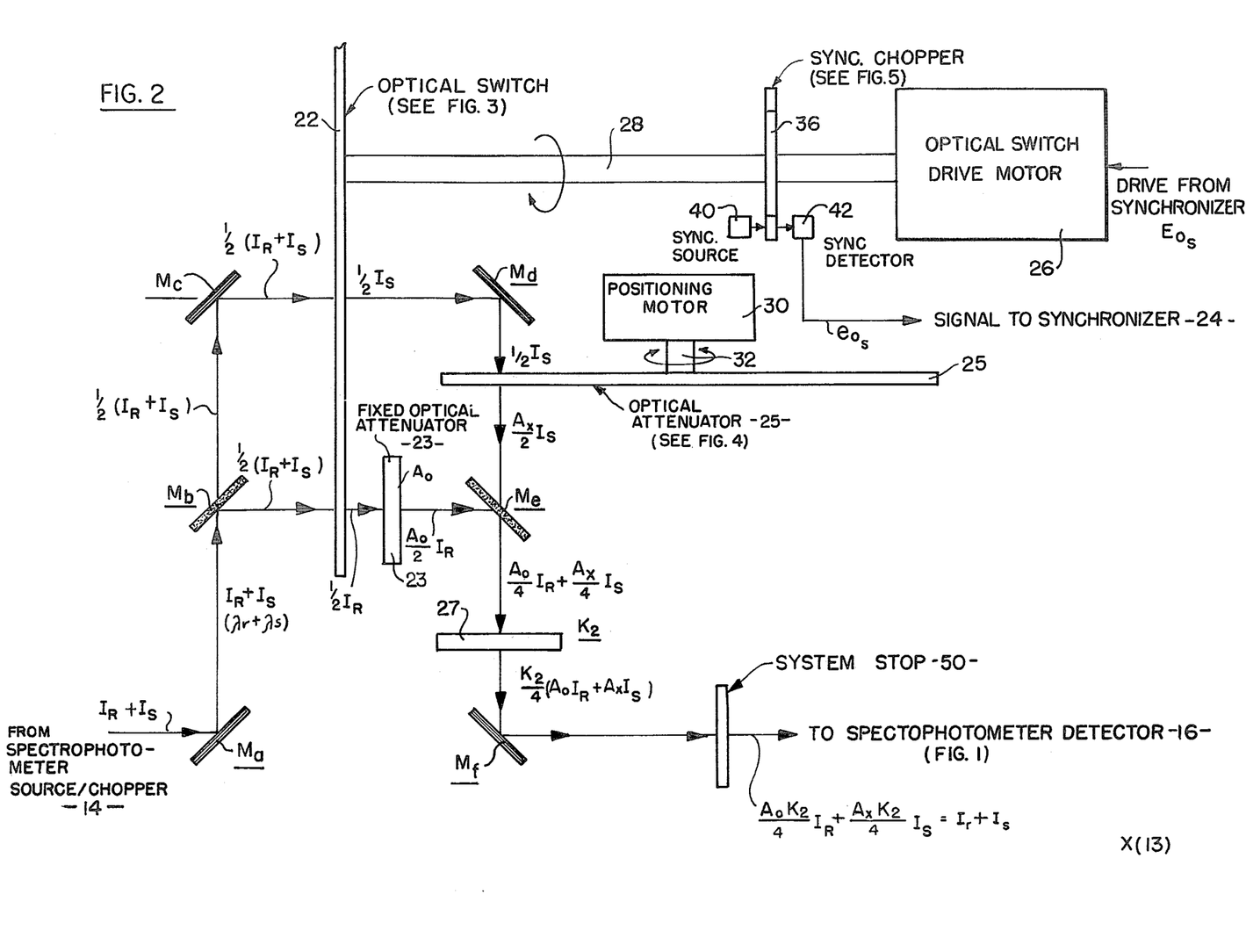
FIG. 2 is a more detailed schematic representation of the calibration system of the invention, in the embodiment of FIG. 1.
Figure 3:
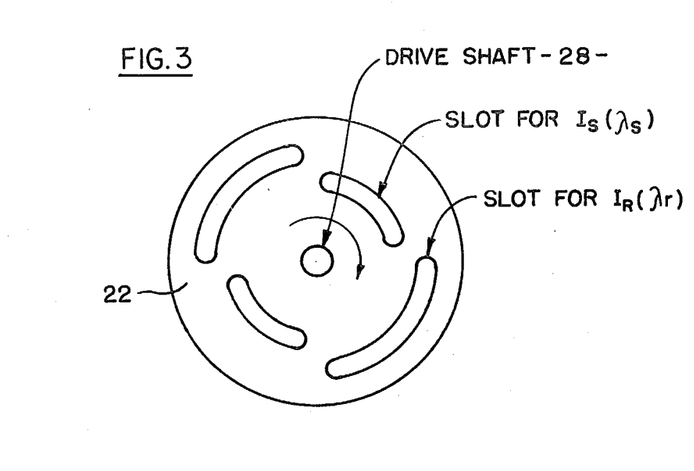
FIG. 3 is a schematic plan view of an optical switch used in the calibration system of FIG. 2.

As shown in FIG. 1, the calibrator system of the invention includes three principal components, namely the optical switch 22, a synchronizer 24, and the optical attenuators 23 and 25. The optical switch 22, as shown in FIGS. 2 and 3 is driven by a drive motor 26 which is coupled to the optical switch by a drive shaft 28. The optical switch is synchronized with the light beams $I_R$ and $I_S$ in the spectrophotometer by the synchronizer 24. The synchronizer 24 responds to the synchronizing signal $e_c$ from the filter chopper 14, and to a synchronizing signal $e_{os}$ from the optical switch 22 to supply a drive signal $E_{os}$ to the optical switch drive motor 26.

In this way, the optical switch is phased so that the reference beam $I_R$ passes through the fixed attenuator 23 ($A_0$), and the sample beam $I_S$ passes through the selectable attenuator 25 ($A_1, A_2, A_3 \ldots$). The selectable attenuator 25 is selectively moved from one angular position to the next by a positioning motor 30 (FIG. 2) which is coupled to the attenuator by a drive shaft 32. The optical filters $A_0, A_1, A_2, A_3 \ldots$ are preferably precision glass neutral density filters. However, by careful design, other attenuators may be used, such as a comb attenuator, an iris diaphragm, and the like.

The attenuated light beams $I_r$ and $I_s$ are then recombined in the calibration system, and focused onto the detector 16 of the spectrophotometer. As stated above, the signals $i_r$ and $i_s$ from the detector are separated in the synchronous demodulator 18, and are then ready for further processing in the computer 20.

A first synchronizing signal $e_c$ is received from the filter chopper of the spectrophotometer and is applied to the synchronizer (and is also used by the demodulator). The second synchronizing signal $e_{os}$ for the synchronizer 24 is developed by a synchronizing signal chopper shutter 36 (FIG. 2) mounted on shaft 28. The chopper shutter 36 is also shown in FIG. 5. A light source 40 is provided which introduces a light beam through the chopper shutter 36 to a detector 42, in the form, for example, of a photo transistor. The detector 42 generates electrical pulses $e_{os}$ in synchronism with the optical switch 22.

The phase relationship between the light beams $I_R$ and $I_S$, as shown in FIG. 6, is determined by the filter chopper 14. The synchronizer applies the drive signal $E_{os}$ to the motor 26 in a manner such that the optical switch 22 is phase-locked with the filter chopper 14 of the spectrophotometer so that the light beams $I_R$ and $I_S$ are gated through the proper attenuator 23 or 25, and the optical switch causes no attenuation of the light beam in the desired path, but blocks the light beam completely in the alternate path. For example, during $I_S$ time there is no attenuation of the light beam between $M_c$ and $M_d$, but during this same time no light is allowed to travel through the optical switch in the direct path between $M_b$ and $M_e$.

It is possible, however, to use the calibration system of the invention with unmodulated monochromatic or white light from source 10. In such an embodiment, the optical switch 22 would be used to chop the unmodulated light beam to synthesize two or more pulsed light beams simulating two or more wavelengths, and the output of the sync chopper 36 would be used to drive the synchronous demodulator 18 of the spectrophotometer. This embodiment would then calibrate the electronics, including the detector 16, but would not calibrate the optical portions of the spectrophotometer.

The optical section of the calibration system is shown in FIG. 2. The optical section includes a mirror $M_a$ at the entrance port to the system, which directs the incoming beam to a semi-transparent mirror $M_b$. One-half of the beam passes through the semi-transparent mirror $M_b$ to a mirror $M_c$ which directs the beams through the optical switch 22 to a mirror $M_d$ which, in turn, directs the beam through a semi-transparent mirror $M_e$ and through an attenuator 27 to a mirror $M_f$. Attenuator 27 contains a neutral density optical filter $K_2$. The latter mirror directs the beams through a system stop 50 to the exit port, through which the beams are passed to the spectrophotometer detector 16 of FIG. 1.

The semi-transparent mirror $M_b$ reflects the beams through the optical switch 22 to the optical attenuator $A_0$, 23, and the beam from the optical attenuator is reflected by the semi-transparent mirror $M_e$ through the optical filter $K_2$ of attenuator 27 to the mirror $M_f$.

When the beam $I_R$ enters the calibration system, the slot $\lambda_r$ in the optical switch 22 is open and the slot $\lambda_s$ is closed. The light beam $I_R$ therefore enters the entrance port, is reflected by the mirror $M_a$, and is reflected by the semi-transparent mirror $M_b$ through the optical switch 22, so that one-half $I_R$ is directed through the optical attenuator 23 ($A_0$) to the semi-transparent mirror $M_e$. The beam directed to the mirror $M_e$ from the attenuator 23 ($A_0$) has the value $(A_0/2)I_R$.

In like manner, when the light beam $I_S$ enters the calibrator, the aperture $\lambda_s$ in the optical switch is opened, so that one-half the $I_S$ beam is directed to the mirror $M_d$ to be reflected through the adjustable attenuator 25 ($A_1, A_2, A_3\ldots$). Assuming that the attenuator 25 is in its first position so that $I_S$ Passes through filter $A_1$, the beam emerging from the attenuator has a value $(A_1/2)I_S$. The latter beam passes through the semi-transparent mirror $M_e$ where it is combined with the beam from the optical attenuator 23 ($A_0$), so that beams having the values $(A_0/4)I_R$ and $(A_1/4)I_S$ are passed through the filter $K_2$ of attenuator 27 to the output reflector $M_f$. The resulting beams are passed through the system stop 50 and introduced to the spectrophotometer detector 16, the beams having the value of $A_0(K_2/4)I_R$ and $A_1(K_2/4)I_S$.

In order to simplify the description of the attenuation of the two light beams $I_R$ and $I_S$, it has been assumed that the light beams are perfectly collimated and smaller than the system stop 50, and that no losses occur in the various mirrors. Also, it is assumed that exactly one-half of the light passes through and one-half of the light is reflected at right-angles by the semi-transparent mirrors $M_b$ and $M_e$.

Therefore, the output ratios from the calibration system of FIG. 2 are as follows:

$$I_r/I_s = \frac{\frac{1}{4}(A_0 K_2) I_R}{\frac{1}{4}(A_1 K_2) I_S}.$$

Therefore, $$\text{Log}\,(I_r/I_s) = \text{Log}\,\frac{\frac{1}{4}(A_0 K_2) I_R}{\frac{1}{4}(A_1 K_2) I_S} = \text{Log}\,\frac{A_0}{A_1}\,\frac{I_R}{I_S}.$$

If the spectrophotometer is to be calibrated in absorbance units, this calibration can be accomplished by using two known values for the attenuator 25. Using $A_1$ and $A_2$ at these two values:

$$\text{Spectrophotometer Sensitivity} = \text{Log}\,\frac{A_0}{A_1}\,\frac{I_R}{I_S} -$$
$$\text{Log}\,\frac{A_0}{A_2}\,\frac{I_R}{I_S}$$
$$= \text{Log}\,\frac{A_1}{A_2}.$$

Using additional values for attenuator 25 enables one to make linearity corrections, or to develop a calibration curve of absorbance versus spectrophotometer output. Increasing $K_2$ simulates more opaque sample cell conditions. This enables the development of a whole series of absorbance curves.

Figures 7, 8, 9:
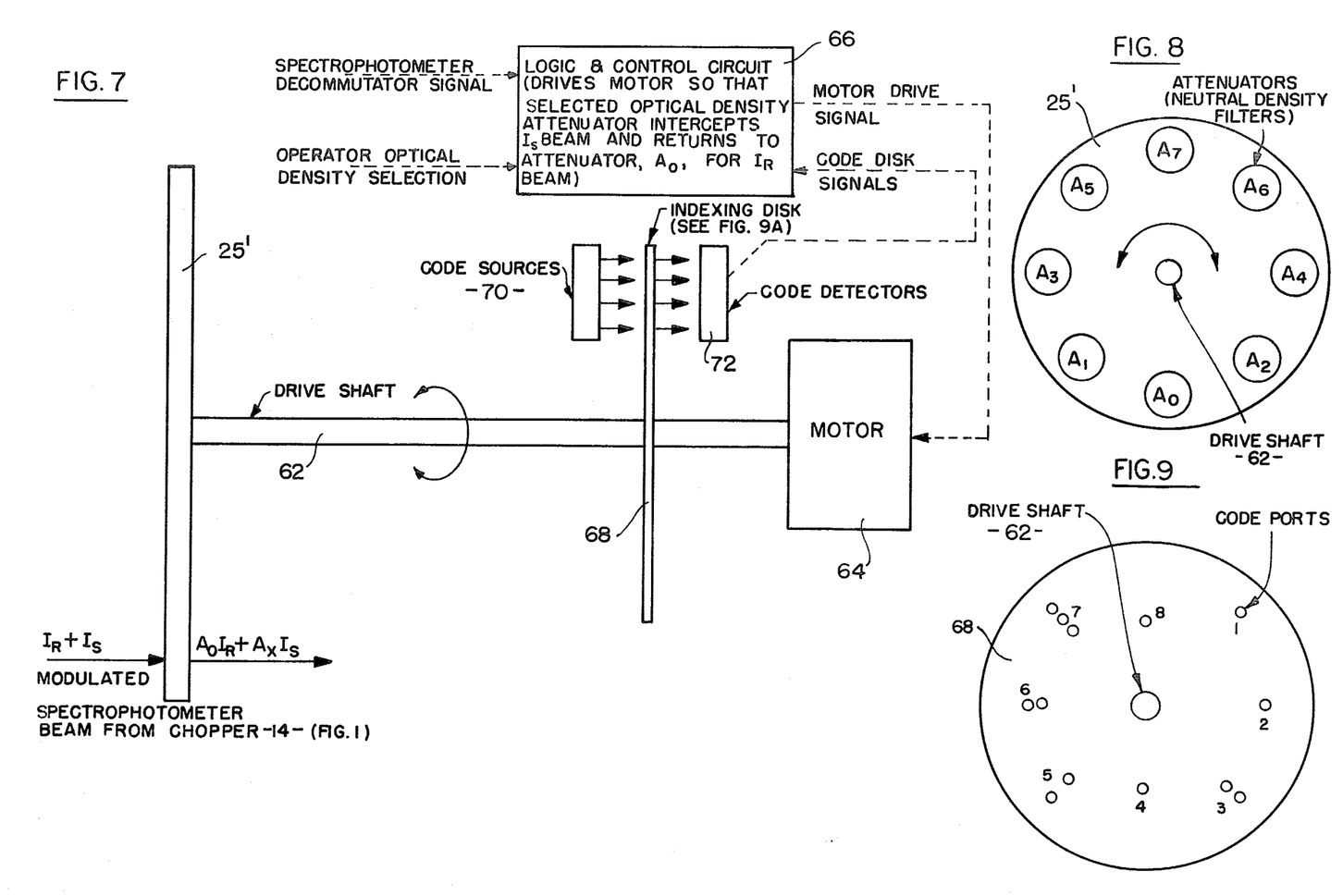
FIGS. 7-13 are representations of various components of further embodiments of the calibration system of the invention.

A second embodiment of the calibrator of the invention is shown in FIGS. 7 and 8. In the second embodiment, a positioning motor 64 drives a filter wheel 25' through a reciprocating drive shaft 62, and an indexing disc 68 is mounted on the shaft 62 of the motor. The filter wheel 25' in the second embodiment includes a series of neutral density filters $A_0$–$A_7$ arranged in the order shown in FIG. 8.

Typical values for the attenuators may be as follows:

| Attenuator | Optical Density |
| --- | --- |
| $A_0$ | 0.02 |
| $A_1$ | 0.52 |
| $A_2$ | 1.02 |
| $A_3$ | 1.52 |
| $A_4$ | 2.02 |
| $A_5$ | 2.52 |
| $A_6$ | 3.02 |
| $A_7$ | 3.52 |

The calibration system places the filter $A_0$ in the light beam when $I_R$ passes through the system from chopper 14 of FIG. 1, and places the filter $A_1$ in the light beam when the beam $I_S$ passes through the chopper 14. Likewise, the reciprocating mechanism can be adjusted to place any one of the other filters $A_2, A_3 \ldots A_7$ in the light beam when the beam $I_S$ passes through the chopper 14. The reciprocating mechanism can be any appropriate reciprocating mechanism, for example, it may be a servo motor or reversing stepping motor 64, as shown in FIG. 7.

As shown in FIG. 7, the motor 64 is coupled to the filter wheel 25' through the reciprocating drive shaft 62. The motor 64 is driven by a logic and control circuit 66 which drives the motor so that the selected optical density filter on the filter wheel 25' intercepts the $I_S$ beam, and so that the motor will return the filter wheel 25' to the attenuator $A_0$ for the $I_R$ beam. The logic and control circuit 66 responds to a decommutator signal from the spectrophotometer, and to a signal designating the filter to be selected by the filter wheel 25'. The motor 64 also drives the indexing disc 68 which is shown in FIG. 9, and which introduces optical signals from appropriate code sources 70 to a series of photodetectors 72, so that the code detectors may introduce corresponding electrical signals to the logic and control circuit 66.

Figure 10:
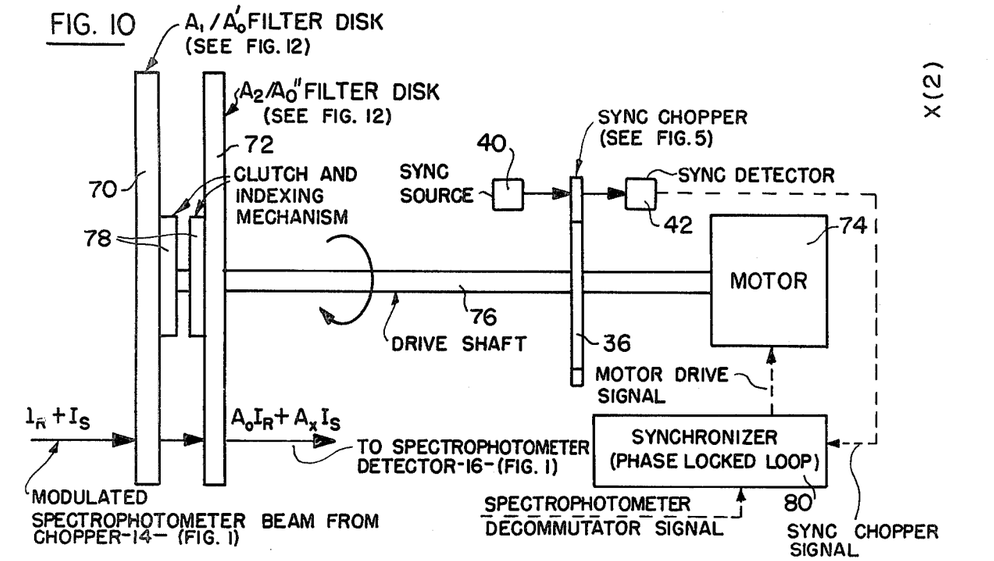
Figure 11:
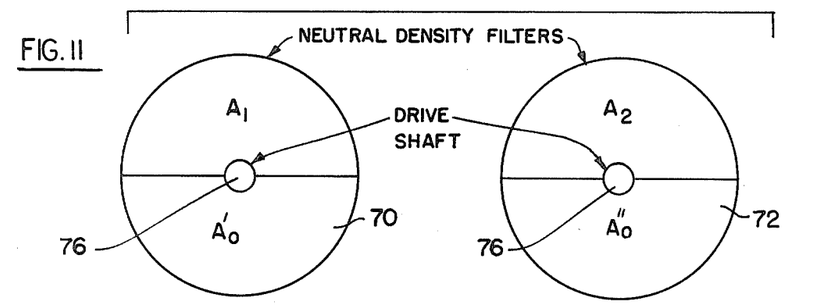

A further embodiment of the calibration system of the invention is shown in FIGS. 10–13. The embodiment of FIGS. 10–13, like the embodiment of FIG. 7, moves neutral density filters into the common light beam in synchronism with the light beams $I_R$ and $I_S$. However, the embodiment of FIGS. 10–13 does not require a reciprocating motor drive, but functions at a constant rotation of the filter wheels, such as in the first embodiment. In the embodiment of FIGS. 10–13, a pair of filter discs 70 and 72 are driven by a drive motor 74 through a drive shaft 76, the two discs being intercoupled by a clutch and indexing mechanism 78 (FIG. 10). The disc 70 has two neutral density filters $A_1$ and $A_0'$ mounted on it in the configuration shown, and disc 72 has two neutral density filters $A_2$ and $A_0''$ mounted on it in the illustrated configuration.

The system of FIG. 10 operates in the following manner: initially the motor 74 is turned off, and both light beams $I_R$ and $I_S$ pass through the filter $A_0'$ on the disc 70 and $A_0''$ on disc 72. The motor then turns the disc 70 in synchronism with the pulsed light beams, with the beam $I_R$ continuing to pass through filters $A_0'$ and $A_0''$, and with the beam $I_S$ passing through filters $A_1$ and $A_0''$. The value of $A_1$ may be changed to $A_2$ by the clutch mechanism 78 which picks up the second filter wheel and which then rotates a second filter $A_2$ in parallel with $A_1$. Thus, with the two discs, it is possible to obtain three ratios, which is sufficient information to calibrate most spectrophotometers as it provides the information necessary to balance the spectrophotometer, set the instrument sensitivity, and adjust for instrument off-sets.

The synchronizing chopper 36 is driven by the motor 74 in the embodiment of FIG. 10, and the resulting synchronizing signal from the detector 42 is introduced to a synchronizer 80 which is in the form of a phase-locked loop, and which responds to the spectrophotometer decommutator signal to assure that motor 74 drives the discs 70 and 72 in synchronism with the chopped beams $I_R$ and $I_S$.

Figures 12, 13:
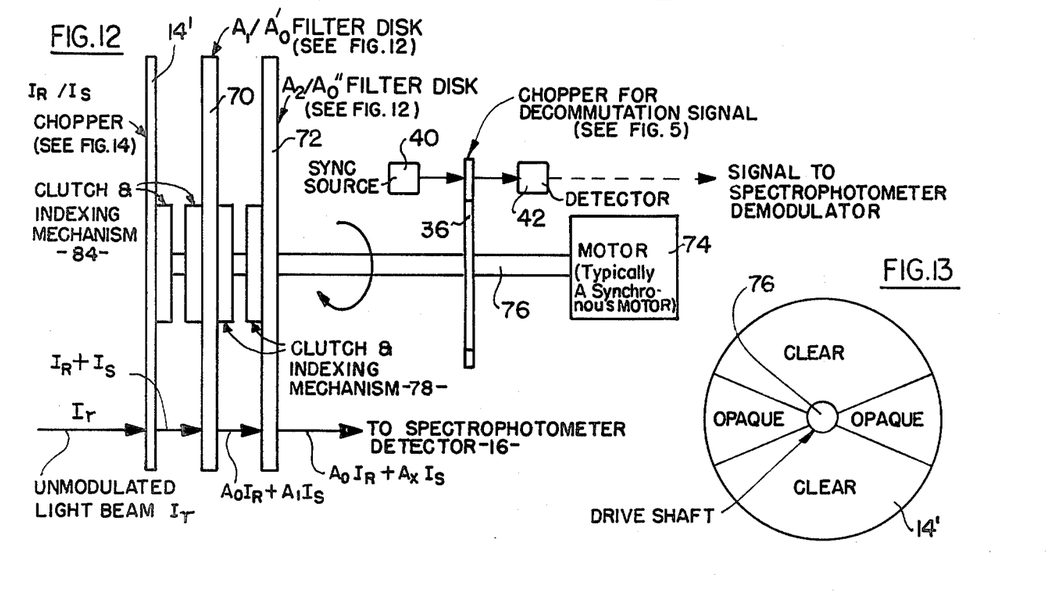

A variation of the system of FIG. 10 is shown in FIG. 12, in which the beam chopper 14' is also driven by shaft 76 through a clutch and indexing mechanism 84. The chopper 14' has the configuration shown in FIG. 13. In the embodiment of FIG. 12, the unmodulated light beam $I_T$ is passed through the chopper 14' where it forms the beams $I_R$ and $I_S$, and the latter beams are then processed by the discs 70 and 72, as in the previous embodiment. The chopper 14' of FIG. 13 converts the light beam into the simulated $I_R$ and $I_S$ light beams which follow each other sequentially, and which are separated by dark periods. Square wave electrical synchronizing signals are generated by the calibrator's sync detector 42 with the transitions occurring during the dark periods between $I_R$ and $I_S$. The resulting square wave signal is applied to the demodulator 18 of FIG. 1. This configuration does not check the total optical system of the spectrophotometer, but it provides a means for calibrating the detector 16 and the spectrophotometer's electronics.

The system of FIG. 12 functions as follows: initially only the chopper 14' rotates and both the $I_R$ and $I_S$ pulses pass through the filter $A_0'$ on disc 70 and $A_0''$ on disc 72. The clutch 84 the connects filter disc 70 to the rotating chopper 14' so that the dark periods overlap the filter segment transition. The $I_R$ beam continues to pass through the filter $A_0'$ on disc 70 and $A_0''$ on disc 72, while the $I_S$ beam passes through the filter $A_1$ and $A_0''$. The value of $A_1$ is changed to $A_1 + A_2$ when clutch 78 picks up filter disc 72. Again, the system provides three ratios $A_0/A_0$; $A_0/A_1$; $A_0/(A_1+A_2)$, which is adequate to calibrate most spectrophotometers.

While particular embodiments of the invention have been shown and described, modifications may be made. It is intended in the claims to cover the modifications which come within the spirit and scope of the invention.

What is claimed is:

1. A calibration system for a spectrophotometer of the type which uses at least first and second light beams which pass through a common sample cell, said calibration system comprising: optical attenuation means comprising a first optical attenuator including a neutral density filter of a known attenuation value and a second optical attenuation including a plurality of neutral density filters each of a different known attenuation value; and control means including a first control system coupled to the first and second attenuators selectively to place the filter of the first attenuator in the path of the first of the two light beams and a first one of the filters of the second optical attenuator in the path of the second of the two light beams, and a second control system coupled to the second optical attenuator selectively to replace the first filter of the second optical attenuator with successive ones of the filters thereof.

2. The calibration system defined in claim 1, in which said second optical attenuator includes at least three neutral density filters each of a different known attenuator value, and said second control system serves to replace the first filter of the second optical attenuator with a second one of the filters thereof, and subsequently to replace the second filter of the second optical attenuator with a third one of the filters thereof.

3. The calibration system defined in claim 1, in which the two light beams of the spectrophotometer pass sequentially through the sample cell along a common path, and in which said calibration system includes a synchronizer responsive to a synchronizing signal from the spectrophotometer for causing said first control system selectively to direct one of the light beams to the first attenuator and the other of the light beams to the second attenuator.

4. The calibration system defined in claim 3, in which said first control system includes an optical switch.

5. The calibration system defined in claim 4, in which said optical switch includes a disc, and a motor coupled to the disc for rotatably driving the disc in synchronism with the occurrence of the respective ones of the two beams of the spectrophotometer.

6. The calibration system defined in claim 1, in which said second control system includes a positioning motor coupled to the second attenuator for rotating said second attenuator from one angular position to another selectively to place the neutral density filters thereof in the path of the other of the two light beams.

7. The calibration system defined in claim 1, and which includes a further optical attenuation means including at least one neutral density filter of known attenuation value positioned in the path of both of the beams of the spectrophotometer.

8. The calibration system defined in claim 1, in which said optical attenuation means comprises a disc having said filters mounted thereon at selected angular positions; and said control means includes a motor synchronized with the spectrophotometer for reciprocally turning the disc so as to place a first one of the filters in the path of one of the light beams and a second one of the filters in the path of the other of the light beams.

9. The calibration system defined in claim 8, in which said motor reciprocally turns said disc.

10. The calibration system defined in claim 9, in which said control means further includes means selectively to cause the motor to turn the disc to place any selected one of a plurality of said filters on the disc other than said first filter in the path of the other of the light beams, and to place the first filter in the path of said one of the light beams.

11. The calibration system defined in claim 1, in which said disc has a first one of said filters on one arcuate half thereof and a second one of said filters on the other arcuate half thereof, and in which said motor imparts rotational movement to said disc so as to place said first one of the filters in the path of one of the light beams and said second one of the filters in the path of the other of the light beams.

12. The calibration system defined in claim 11, in which said optical attenuation means comprises a second disc positioned in concentric relationship with said first disc to be driven by said motor, said second disc having a third one of said filters on one arcuate half thereof to be positioned adjacent said second one of said filters on the first-named disc.

13. The calibration system defined in claim 12, and which includes a third disc mounted concentrically with the second disc to be driven by said motor, said third disc having clear and opaque segments thereon to function as a light chopper to establish the two light beams in the spectrophotometer.

14. The calibration system defined in claim 1, in which said control means includes a first control system including an optical switching member coupled to said attenuation means and responsive to an unmodulated light beam to synthesize at least two pulsed light beams simulating at least two wavelengths.

* * * * *